United States Patent [19]

Kim et al.

[11] Patent Number: 5,055,586

[45] Date of Patent: Oct. 8, 1991

[54] DESULFURIZATION OF TRIAZOLOTHIADIAZINES

[75] Inventors: Chang K. Kim, Pittsford; Wayne N. Lamicela, Rush; David L. Allen, Holcomb, all of N.Y.

[73] Assignee: Eastman Kodak Company, Rochester, N.Y.

[21] Appl. No.: 527,982

[22] Filed: May 24, 1990

[51] Int. Cl.⁵ .......................................... C07D 487/04
[52] U.S. Cl. .................................................. 548/262.4
[58] Field of Search ...................................... 548/262.4

[56] References Cited

FOREIGN PATENT DOCUMENTS 284239   9/1988  European Pat. Off. ......... 548/262.4
63-101386  5/1988  Japan ............................... 548/262.4
63-101387  5/1988  Japan ............................... 548/262.4

Primary Examiner—Mary C. Lee
Assistant Examiner—Patricia L. Morris
Attorney, Agent, or Firm—Robert A. Linn

[57] ABSTRACT

Pyrazolotriazoles such as 3,6-disubstituted-1H-pyrazolo[5,1-c]-1,2,4-triazoles:

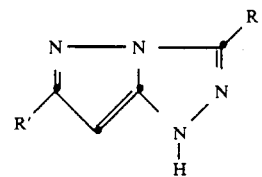

are useful in the photographic arts, e.g. as magenta couplers. They may be made from 3,6-disubstituted-7H-1,2,4-triazolo[3,4-b][1,3,4]thiadiazines:

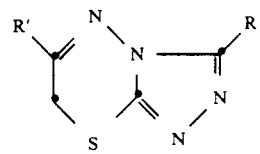

by a two-step process. The first step comprises a ring contraction and a diacylation. The second step comprises hydrolysis of the acyl groups and desulfurization. The second step is conducted using an aqueous mixture of a hydrohalic acid such as hydrochloric acid and hypophosphorous acid, $H_3PO_2$. When the hypophosphorous acid is used, less sulfur and sulfur-containing impurities are formed.

7 Claims, No Drawings

DESULFURIZATION OF TRIAZOLOTHIADIAZINES

FIELD OF THE INVENTION

This invention relates to an improved process for the deacylation and desulfurization of a compound having the formula:

(III)

In the improved process of this invention hypophosphorous acid is employed in the deacylation and desulfurization to improve product yield and reduce the yield of unwanted impurities.

BACKGROUND OF THE INVENTION

Pyrazolotriazoles, such as those described herein are useful magenta couplers for photographic products. However, they are difficult to synthesize. Only a few synthetic routes are known. One of the preferred synthetic routes involves preparation of the triazolothiadiazines 1 and subsequent desulfurization reaction to give the pyrazolotriazoles 2. The triazolothiadiazines 1 can be prepared in two ways; the first, by reaction of 4-amino-5-mercapto-3-substituted(R)-1,2,4-triazoles (4) with alpha-haloketones, or the second, by reaction of 2-hydrazino-5-substituted-(R')-1,3,4-thiadiazines (5) with acyl halides and subsequent dehydrative ring closure. Both the triazoles 4 and the thiadiazines 5 are readily available from thiocarbohydrazide;

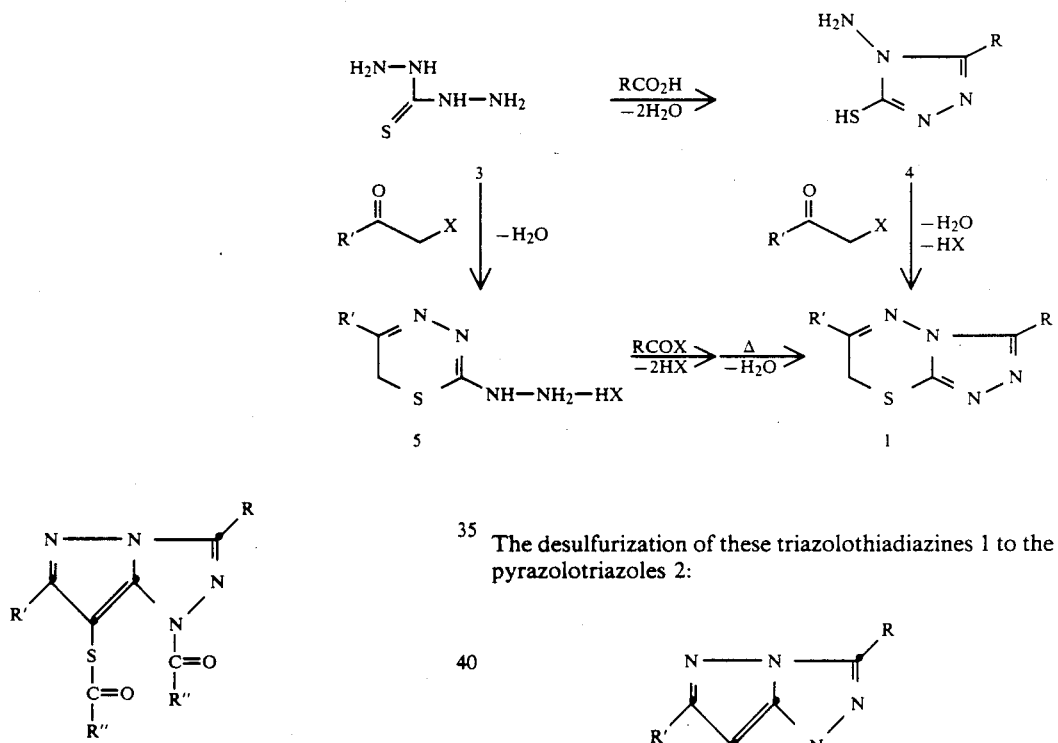

The desulfurization of these triazolothiadiazines 1 to the pyrazolotriazoles 2:

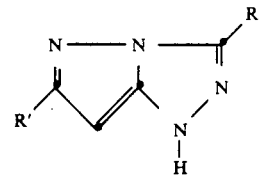

is effected in two steps; the first, a ring contraction reaction of 1 by heating in acetic anhydride to give 1-acetyl-7-acetylthio-3,6-disubstituted-1H-pyrazolo[5,1-c]-1,2,4-triazoles (6) and, the second, hydrolysis of acetyl groups and desulfurization at the same time with hydrochloric acid to give the desired 2.

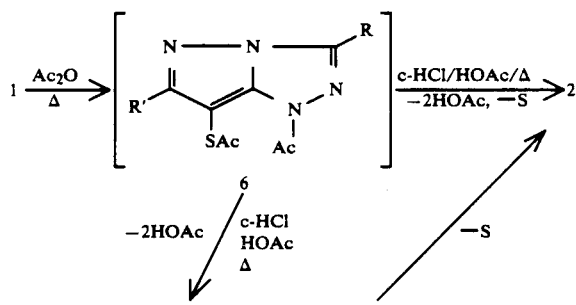

-continued

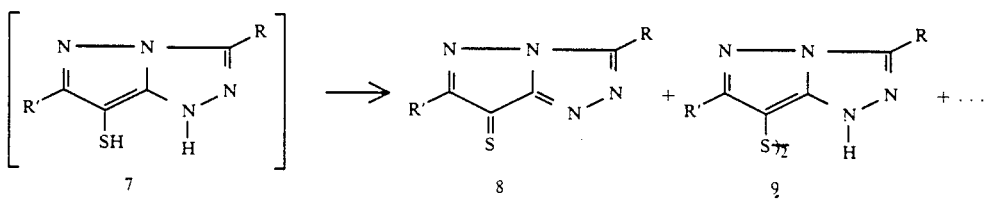

Although this is the most attractive and practical method for desulfurization among those available, there are several drawbacks in using this as a manufacturing process. The first ring contraction reaction is usually clean and does not render any problem except long reaction time. In fact, the reaction mixture is clean enough to be used in the next step without isolation of 6. However, the subsequent reactions are not straight-forward. The hydrolysis and desulfurization reactions with hydrochloric acid generate not only elemental sulfur as by-product but also many sulfur-containing organic impurities. Among them are two major impurities identified as thione 8 and disulfide 9. These oxidized forms of mercapto intermediate 7 seem to result by the action of elemental sulfur formed during the reaction of 7.

Not only elemental sulfur, but also the sulfur-containing organic impurities are considered detrimental. They can interfere with subsequent reaction steps, e.g. a catalytic hydrogenation of a nitro group on one of the groups R or R' in the above formulae. Also, sulfur is a potential fogger in photographic systems.

Because the process of this invention makes much smaller amounts of these detrimental impurities, and is straight-forward and readily carried out, it is considered to be a significant advance in the art.

SUMMARY OF THE INVENTION

This invention relates to an improved process for the preparation of certain pyrazolotriazoles from their triazolothiadiazine precursors. The improvement comprises a deacylation and desulfurization step conducted in the presence of hypophosphorous acid. Use of hypophosphorous acid reduces the amount of elemental sulfur and the amounts of sulfur-containing organic impurities which are formed when hypophosphorous acid is not used in the reaction mixture.

For example, if hypophosphorous acid is not used in a process for making the compound produced in Example 1, hereinbelow, the thione and disulfide impurities corresponding to formulas 8 and 9 can be produced in significant levels; 5–15 area percent as determined by LC/MS (liquid chromatography/mass spectrographic analysis). Without the hypophosphorous acid, the product of Example 1 is prepared in comparatively low yield, 45–50%. Apparently, the low yield is due to formation of the undesired impurities mentioned above.

In contrast, when the process of Example 1 is used, the desired pyrazolotriazole can be produced in 82% yield and with a purity of 98 area % by HPLC (high pressure liquid chromatography).

The use of hypophosphorous acid in the process of this invention has several advantages besides reducing the amounts of undesirable by-products and increasing the yield of the desired product. For example, use of hypophosphorous acid results in formation of H₂S by-product rather than sulfur. In view of the gaseous nature of H₂S and its chemical reactivity, it is readily removed from the reaction zone and trappel, for example, by caustic and sodium hypochlorite. Furthermore, hypophosphorous acid does not reduce nitro groups which are commonly present on side chains in photographic intermediates, or affect other functional groups in the molecule.

In summary, this invention overcomes significant difficulties and provides several advantages. For these reasons, and because the process is straight-forward and economical to carry out, it is readily adaptable by industry.

DESCRIPTION OF PREFERRED EMBODIMENTS

In a preferred embodiment, this invention provides the process for the preparation of a 3,6-di-substituted-1H-pyrazolo[5,1-c]-1,2,4-triazole having the formula:

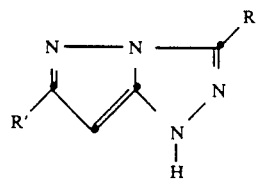

said process comprising reacting an acylated compound having the formula:

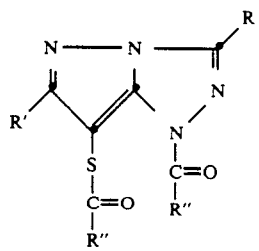

with an aqueous mixture of hypophosphorous acid and hydrochloric acid or hydrobromic acid to produce hydrogen sulfide and said pyrazolotriazole;

R and R' and R" being inert substituents;

said process being characterized by generating less sulfur and sulfur-containing organic impurities than when no hypophosphorous acid is present.

In another preferred embodiment, this invention provides a process for the preparation of a 3,6-di-substituted-1H-pyrazolo[5,1-c]-1,2,4-triazole having the formula:

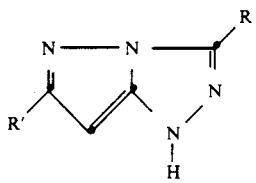

from a 3,6-disubstituted-7H-1,2,4triazolo[3,4-b]-[1,3,4]thiadiazine having the formula:

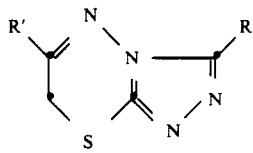

wherein R and R' are alike or different and are selected from photographically acceptable, inert substituents;

said process comprising: (i) reacting compound (I) with an acylating agent to form an acylated intermediate

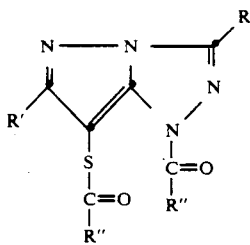

and (ii) subsequently reacting said acylated intermediate with an aqueous mixture of hypophosphorous acid and hydrochloric acid or hydrobromic acid to produce hydrogen sulfide and pyrazolotriazole (II);

said process being characterized by generating less sulfur and sulfur-containing organic impurities than when no hypophosphorous acid is present in step (ii).

In the compounds used as starting materials in this invention, and the compounds produced as intermediates, as well as the desired products, all represented by Formulas 1-9 above, R and R' are "inert substituents".

For the purpose of this invention, an "inert substituent" or "inert organic group" is defined by having the following characteristics:
(1) It is stable, or substantially stable, under the process conditions employed: i.e. it does not decompose to an untoward extent during process(es) employed in this invention.
(2) It is non-reactive, or substantially non-reactive toward the other reagents employed, i.e. it does not undergo an extraneous side reaction (to an unacceptable extent) with the other ingredient(s) used.
(3) It does not prevent, by steric hindrance or other mechanism or effect, the formation of a compound of this invention.

Thus, a wide variety of substituents may appear as R and/or R' in the above formulas. In other words, this invention is not critically dependent on the type(s) of groups designated R and R', so long as the groups meet criteria (1), (2) and (3) above. Typically, R and R' are hydrocarbyl groups, i.e. groups which are solely composed of carbon and hydrogen. However, it is not necessary that R and R' be solely composed of carbon and hydrogen; thus groups which comprise:

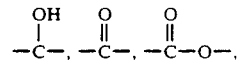

NO$_2$, —NH$_2$, NHR, NRR, —SO$_2$—, —S—, and alkoxy, aryloxy, the like, can appear in compounds of this invention, so long as the substituents meet the three criteria enumerated above. Alkyl, cycloalkyl, alkenyl, cycloalkenyl, aryl, aralkyl, heteroaryl groups and heterocyclic groups containing oxygen, sulfur or nitrogen as the heteroatom which meet the above criteria can be present in the compounds of this invention. These may be hydrocarbyl, or substituted hydrocarbyl groups, as discussed above. For convenience, R and R' are usually hydrocarbyl groups having up to about 20 carbon atoms; preferably they are hydrogen or alkyl or aryl groups of this type.

When the radical R'' appears in compounds of this invention, it represents lower alkyl radicals, preferably those having up to about 6 carbon atoms. In compounds of this invention R and R' may be alike or different.

The R, R' and R'' radicals are generally selected according to the properties that they confer on the compounds, and/or the role that they play in the selected utility. For example, since the radical R'' appears in a group which is to be subsequently removed by hydrolysis, R'' is preferably selected from a methyl or ethyl, or other lower alkyl group having up to about four carbon atoms in order to lower process costs.

On the other hand, the size or nature of the group may be selected because it is produced in a convenient reaction for preparing the pyrazolotriazole starting compound, or the group may be selected to confer some physical or chemical property, such as a desired degree of solubility, or a desired degree of compatibility with other ingredients in a mixture in which the product is used.

Moreover, one or more of the radicals R and R' may be selected to contain a radical which contains a reactive site. For example, R may be a group having the formula:

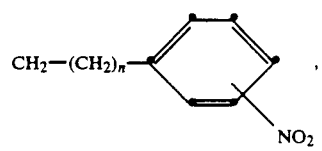

wherein n is a whole number equal to 0 to about 6, and the nitro group is ortho, meta or para to the alkyl side chain. For some uses, it is desirable to subsequently reduce the aryl nitro group to an amino group. Accordingly, it is to be understood that the term "inert" in the phrase "inert substituent" does not mean that the substituent is unreactable in processing conducted after the compound is made.

As indicated above, compound (III) can be prepared by an acylation reaction. For the acylation an anhydride having the formula:

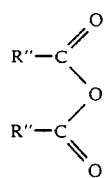

is employed.

The acylating agent may be used in solvent quantities. There is no real upper limit on the amount of acylating agent; this being defined by such secondary characteristics as economics, size of the reaction vessel, ease of separation of product from the reaction mixture, ease of recovery of the unreacted acylating agent, etc.

The process may be conducted in the presence of a catalytic quantity of a Bronsted or Lewis acid. For the purpose of this invention, a Bronsted acid is any proton donor which donates a proton and does not hinder the process. Such materials are generally selected from alkyl sulfonic acids, hydrogen halides, sulfuric acid, and carboxylic acids such as those acids mentioned above for use as acylating agents. Lewis Acids, such as those employed for Friedel-Crafts acylations, e. c. $AlCl_3$, $FeCl_3$ $BF_3$, HF, $H_3PO_4$ and the like, can also be used as catalysts.

Generally speaking, a catalytic amount of such catalyst, e.g. from about 0.05 to about 0.25 moles per mole of starting triazolothiadiazine is used. Greater or lesser amounts can be employed if they afford the desired result.

The acylation may be conducted at any convenient temperature which gives a reasonable rate of reaction, and which does not cause an undue amount of decomposition of one or more of the ingredients employed. Generally speaking, a temperature within the range of from about 20° C. to about 200° C. is employed; more preferably the temperature is from about 100° C. to about 150° C.

Ambient pressure is generally satisfactory. Higher pressures, up to 100 atmospheres or more can be used if one of the reagents is a gas or vapor at the reaction temperature.

The process is generally conducted in the substantial absence of water or with a small amount of water to prevent unwanted hydrolysis.

The reaction time is not a completely independent variable, but is dependent at least to some extent on the other reaction conditions employed, and the inherent reactivity of the reactants. In general, higher reaction temperatures require shorter reaction times. The process is usually complete in from about 0.5 to about 24 hours.

After the acylation has been conducted, it may be desirable to add water to the reaction mixture in order to hydrolyze any excess acid anhydride. The water addition may be accompanied by agitation of the reaction mixture (e.g. by stirring) to facilitate hydrolysis.

After any hydrolysis is conducted as discussed in the paragraph immediately above, the deacylation and desulfurization reaction can be conducted on the reaction mixture produced. In other words, it is not necessary to isolate compound (III) in order to conduct the next step. Although isolation is not necessary, it can be carried out if desired, using techniques within the skill of the art, e.g. fractional crystallization, distillation, extraction and the like.

The deacylation and desulfurization is generally conducted at a temperature which gives a reasonable rate of reaction, but which does not cause unwanted, extraneous side reactions to take place with loss of yield of desired product. For example, temperatures of from 50° to 100° C. can be employed; generally it is preferred to use a temperature of from 70°–90° C.

Ambient pressures are preferred; however, somewhat elevated pressures can be used if the reaction is to be conducted at a temperature above the boiling point of one or more of the constituents in the reaction mixture.

The deacylation/desulfurization is generally conducted using a hydrochloric acid or hydrobromic acid. In general, the amount of acid is at least stoichiometric; however, an excess of acid can be employed if desired. The amount of hypophosphorous acid ($H_3PO_2$) employed is preferably at least equimolar with the thiadiazine. However, additional $H_3PO_2$ can be used if desired.

The reaction time is not a truly independent variable, but is at least somewhat dependent on the reaction temperature and the inherent reactivity of the reactants. In general, reaction times of from 0.5 to 10 hours are sufficient.

After the desulfurization reaction is complete the desired pyrazolotriazole can be isolated from the reaction mixture by a known technique such as extraction, as indicated by the following examples.

EXAMPLE 1

6-Methyl-3-[1-(4-nitrophenoxy)tridecyl]-1H-pyrazolo-[5,1-c]-1,2,4-triazole

A mixture of 47.4 g (0.10 m) of 6-methyl-3-(1-[4-nitrophenoxy]tridecyl)-7H-1,2,4-triazolo[3,4-b]-[1,3,4]thiadiazine (1a) and 150 g of acetic anhydride is heated under reflux for 7 hours and left at room temperature over night. Acetic acid (30 g) is added and the mixture is heated to 60° C. A solution of 12.5 g of c-HCl (36%) in 15 ml of water is then added over 20 minutes to assure that hydrolysis of acetic anhydride is complete.

The mixture is cooled to 30° C. and there is added 50.8 g of c-HCl, 13.2 g of 50% hypophosphorous acid, and 56 ml of water. The mixture is slowly heated to 85° C. and stirred at that temperature for 3 hours. During the heating period a gentle gas evolution occurs. The gas is passed through a pre-scrubber solution made of caustic and sodium hypochlorite. The product is extracted with 210 ml of toluene at 65° C. and the toluene solution is washed with hot water (65° C.) 4–5 times to remove acids. While keeping the temperature at 65°–70° C., 230 ml of hot heptane (65° C.) is added and the mixture is cooled slowly without stirring to room temperature. The crystallized product is collected, washed well with 1:1 mixture of toluene and heptane, and dried to give 36.2 g (82%) of 6-methyl-3-[1-(4-nitrophenoxy)-tridecyl]-1H-pyrazolo-[5,1-c]-1,2,4-triazole(2a) with 98 area % by HPLC.

EXAMPLE 2

6-t-Butyl-3-(3nitro-2,4,6-trimethylphenyl)-1h-pyrazolo-[5,1-c]-1,2,4-triazole (2b)

With 6-t-butyl-3-(3-nitro-2,4,6-trimethylphenyl)-7H-1,2,4-triazolo-[3,4-b][1,3,4]thiadiazine (1b), the reaction is carried out as Example 1. After the reaction is complete, the reaction mixture is filtered while hot and drowned out into the water. The precipitated product is collected, washed well with water, and dried. It is slurried in 1:1 mixture of toluene and heptane, and dried again to give the product 2b in 78% yield with 98 area % by HPLC.

In the following example, all parts are by weight.

EXAMPLE 3

A suitable glass-lined reactor is purged with nitrogen to less than 8% oxygen. Thereafter 669 parts of 6-methyl-3-[1-(4-nitrophenoxy)-tridecyl]-7H-1,2,4-triazolo[3,4-b][1,3,4]thiadiazine is charged to the reactor. Thereafter 238 parts of acetic anhydride is metered into the reactor. The agitator is started and the contents heated to 133° C. by using 140° C. steam applied on the jacket. The reaction mixture is maintained at 133° C. for 20 hours. Thereafter, the batch is cooled to 50° C. and sampled for completeness of reaction. If the reaction is complete (less than 2.0% of starting thiadiazine) the batch is cooled and pumped to a receiver or transferred directly to a second reactor.

Hydrochloric acid, 32%, 1690 parts, and 412 parts of 50% hypophosphorous acid are admixed in a reactor receiver. A solution of 100 parts of 32% hydrochloric acid and 1500 parts of filtered water is prepared in the second reactor and heated to 70° to 80° C. Two reaction batches prepared as above and containing the non-isolated 1-acetyl-7-acetylthio-6-methyl-3-(1-[4-nitrophenoxy]tridecyl)-1-H-pyrazolo(5,1-c)-1,2,4-triazole are cautiously transferred to the second reactor while maintaining the contents temperature at 70°-80° C. The hydrochloric acid/hypophosphorous acid solution in the receiver is charged to the second unit at such a rate as to maintain the batch at a temperature less than 80° C. The resultant reaction mixture is maintained at 75°-80° C. for an additional three hours by applying tempered water on the jacket.

Off gasses are vented to an appropriate scrubber. The resulting mixture is checked for completeness of reaction and cooled to 65° C.

If the reaction is complete 1500 parts of toluene is added to the reaction mixture while maintaining the temperature at 65°-70° C. The resultant mixture is settled and the bottom aqueous layer discarded. The toluene layer is washed once with water and twice with water containing 50 parts of sodium chloride. All washes contained 5000 parts of filtered water. During the washings the temperature is maintained at 65°-70° C.

To the washed toluene layer is added 4800 parts of heptane while maintaining the temperature at 70°-75° C. The resultant mixture is then seeded using 20 parts of 6-methyl-3-[1-(4-nitrophenoxy)-tridecyl]-1-H-pyrazole(5,1-c)-1,2,4-triazole. The resultant mixture is then cooled to 18°-22° C. and held at that temperature for 30 minutes.

The resultant mixture is then filtered and the product cake washed with heptane and toluene (1500 parts of each) and then dried and packaged in drums with clear plastic liners.

A suitable stainless steel or glass lined reactor is purged with nitrogen to less than 8% oxygen. Thereafter toluene, 4,040 parts is metered into the reactor and the agitator started. One entire batch of crude 6-methyl-3-[1-(4-nitrophenoxy)-tridecyl]-1-H-pyrazole(5,1-c)-1,2,4-triazole, approximately 900 parts, is charged to the reactor and the batch heated to 70°-75° C. using steam. The batch is maintained in that temperature range for one hour. An additional 4,040 parts of heptane is metered into the batch while maintaining the batch temperature at 70°-75° C. The resultant solution is then cooled to 69° C. and seeded using 20 parts of recrystallized 6-methyl-3-[1-(4-nitrophenoxy)-tridecyl]-1-H-pyrazole(5,1-c)-1,2,4-triazole. The batch is then cooled in a controlled manner to 18°-22° C. and held at 18°-22° C. for 30 minutes. The batch is filtered and the cakes are washed with a mixture of 1500 parts of heptane and 1500 parts of toluene. There is recovered recrystallized 6-methyl-3-[1-(4-nitrophenoxy)tridecyl]-1-H-pyrazole (5,1-c)-1,2,4-triazole.

The invention has been described above with particular reference to preferred embodiments thereof. A skilled practitioner, aware of the above detailed description can make many modifications or substitutions without departing from the scope or spirit of the following claims.

We claim:

1. In a process for the preparation of a 3,6-disubstituted-1-H-pyrazolo[5,1-C]-1,2,4-triazole from the corresponding 1-acyl-7-acylthio-3,6-disubstituted-1-H-pyrazolo[5,1-C]-1,2-4-triazole by hydrolysis of acyl groups and desulfurization; the improvement which comprises conducting the hydrolysis and desulfurization in the presence of hypophosphorous acid, whereby less elemental sulfur and sulfur-containing impurities are formed.

2. In a process for the preparation of a 3-6-disubstituted-1H-pyrazolo[5,1-C]-1,2,4-triazole from the corresponding 3,6-disubstituted-7H-1,2,4-triazolo[3,4-b][1,3,4]thiadiazene by ring contraction and diacylation with an acylating agent, followed by hydrolysis and desulfurization of the acylated intermediate in the reaction mixture in which it is produced; the improvement comprising conducting the hydrolysis and desulfurization in the presence of hypophosphorous acid, whereby less elemental sulfur and sulfur-containing impurities are formed.

3. Process of claim 2 wherein 6-methyl-3-(1-[4-nitrophenoxy]tridecyl)-7H-1,2,4-triazolo[3,4-b]-[1,3,4]thiadiazine] is reacted with acetic anhydride, and the acylated intermediate thereby produced is reacted with HCl in the presence of hypophosphorous acid to produce 6-methyl-3-[1-(4-nitrophenoxy)tridecyl]-1H-pyrazolo-[5,1-c]-1,2,4-triazole.

4. Process of claim 2 wherein 6-t-butyl-3-(3-nitro-2,4,6-trimethylphenyl)-7H-1,2,4-triazolo-[3,4-b][1,3,4]thiadiazine is reacted with acetic anhydride and the acylated intermediate thereby produced is reacted with HCl in the presence of hypophosphorous acid to produce 6-t-butyl-3-(3-nitro-2,4,6-trimethylphenyl)-1h-pyrazolo-[5,1-c]-1,2,4-triazole.

5. Process of claim 2 wherein said acylating agent is an acid anhydride.

6. Process of claim 5 wherein said anhydride is acetic anhydride.

7. Process of claim 2 wherein the amount of hypophosphorous acid is about 0.5 mole to 5.0 moles per each mole of acylated intermediate.

* * * * *